United States Patent [19]

Smith

[11] Patent Number: 4,675,596
[45] Date of Patent: Jun. 23, 1987

[54] DIGITAL FLUID ANALYZER USING CAPACITIVE SENSING

[75] Inventor: Thomas Smith, Walnut Creek, Calif.

[73] Assignee: Zidex Systems, Walnut Creek, Calif.

[21] Appl. No.: 649,018

[22] Filed: Sep. 10, 1984

[51] Int. Cl.⁴ .......................................... G01R 27/26
[52] U.S. Cl. .............................................. 324/61 QS
[58] Field of Search .......... 324/61 QS, 61 R, 61 QL; 73/61 R, 61.1 R

[56] References Cited

U.S. PATENT DOCUMENTS

| | | | |
|---|---|---|---|
| 2,577,612 | 12/1951 | Fay | 324/61 R |
| 3,215,931 | 11/1965 | Schooley, Jr. | 324/61 QS |
| 3,238,452 | 3/1966 | Schmitt et al. | 324/61 R |
| 3,775,679 | 11/1973 | Abbe | 324/61 R |
| 3,778,707 | 12/1973 | Vogel | 324/61 R |
| 4,228,393 | 10/1980 | Pile | 324/61 QS X |
| 4,240,028 | 12/1980 | Davis, Jr. | 324/61 QS |

FOREIGN PATENT DOCUMENTS 0748218  7/1980  U.S.S.R. ............. 324/61 QS

Primary Examiner—Stanley T. Krawczewicz
Attorney, Agent, or Firm—Walter J. Madden, Jr.; Alan H. MacPherson; Steven F. Caserza

[57] ABSTRACT

Apparatus for determining the dielectric constant of a fluid as a measure of possible contaminants therein. A reference fluid sample having a known dielectric constant is first placed in a capacitive dielectric sensor and then the fluid to be analyzed is placed in the sensor. By comparing the measured values, an indication is provided of the degree of contamination of the analyzed fluid.

2 Claims, 4 Drawing Figures

DIGITAL FLUID ANALYZER USING CAPACITIVE SENSING

BACKGROUND OF THE INVENTION

1. Field of the Invention

The present invention is directed to circuitry and apparatus for detecting the presence of undesirable contaminants in fluids such as motor oil, transmission fluid, machine oil, diesel fuel, etc.

2. Description of the Prior Art

It is well known that contaminants in fluids will cause detectable changes in the dielectric constant of the fluid. These contaminants include, but are not limited to water, wear metals, sulfur, acids, anti freeze, and suspended hydrocarbons and other particulate matter.

Currently, expensive and time consuming chemical laboratory analyses are performed to determine the presence of these contaminants. U.S Pat. No. 301,401, Roof et al. discloses a dielectric constant detector employing a reference cell and a sample cell, each of which has plates therein which form capacitors. A fluid of known dielectric constant is placed in the reference cell while the fluid to be tested is passed through the sample cell. Using a pair of oscillators which apply energy to the cells, a signal indicative of the dielectric constant of the sample fluid is obtained.

SUMMARY OF THE INVENTION

The present digital fluid analyzer provides a field analysis capability that can serve either in lieu of or as a screening for the necessity of chemical analysis of the fluid for contaminants.

Specifically, the digital fluid analyzer encompasses a sensor and associated solid state analog and digital circuitry to measure and display resulting changes in the dielectric constant between a sample of known composition and a test sample. Additionally, since the digital display is directly proportional to the fluid's dielectric constant, it is feasible in many applications to utilize air as the reference "fluid" if the unit has been properly calibrated for the fluid under test.

DESCRIPTION OF THE PREFERRED EMBODIMENT

The sensor consists essentially of a parallel plate capacitor into whose electric field a reference and a fluid to be tested can be placed as the dielectric material. It is well known that the capacitance of such a capacitor is determined principally by the spacing between adjacent plates, surface area of the plates, and the dielectric constant of the area enclosed by the electric field of the plates.

Figure 1:
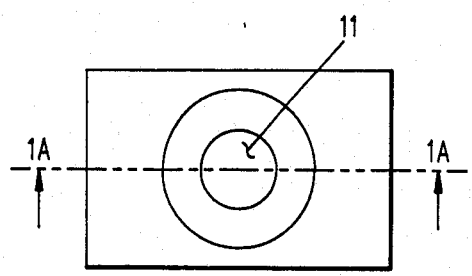
FIGS. 1A, 1B and 1C illustrate the elements of a capacitive sensor which may be employed in the present invention.
Figure 1B:
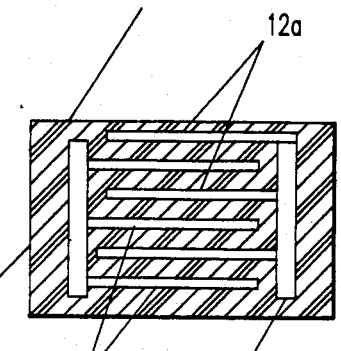
Figure 1A:
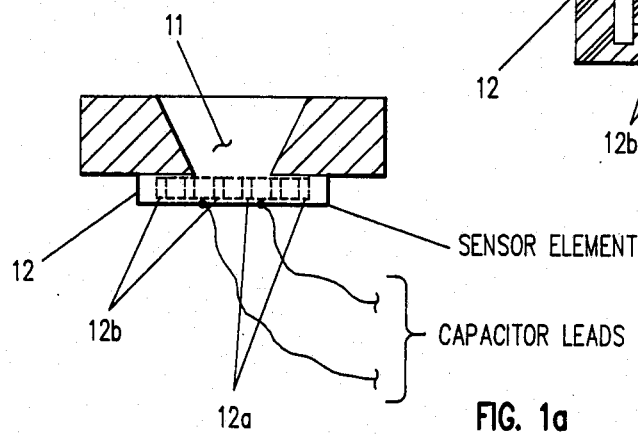

The sensor design utilized for the present digital fluid analyzer consists of two components as shown in FIGS. 1A, 1B and 1C. These components are a fluid well 11 for retaining the fluid in question, and a sensor element comprising the parallel plate capacitor 12 having spaced plates 12a, 12b as shown in FIG. 1C. The size and geometry of the sensor well and sensor element are not especially critical to the operation of the fluid analyzer, since the electronic circuitry can accommodate a wide range of capacitance values.

Dimensions of a prototype unit provide a fluid cup or well volume of approximately 5 cubic centimeters. The sensor element plates are made of copper or other conductor, are between 0.001 inch and 0.004 inch high, and approximately 0.006 inch wide with approximately 0.006 inch spacing between the plates. The overall size of the sensor is approximately 0.5 inch by 0.5 inch.

As previously discussed, the capacitance of the sensor depends on the spacing between the plates as well as the dielectric constant of the fluid. Thus, expansion and contraction of the substrate material 13 to which the copper plates are bonded, as a result of changes in ambient temperature, can introduce undersired changes in sensor capacitance. Thus, the copper plates are bonded to a substrate of fiberglass-epoxy composition or similar material for applications where temperature dependent inaccuracies can be tolerated, or to alumina or low expansion glass where higher temperature range operation is desired.

Figure 2:
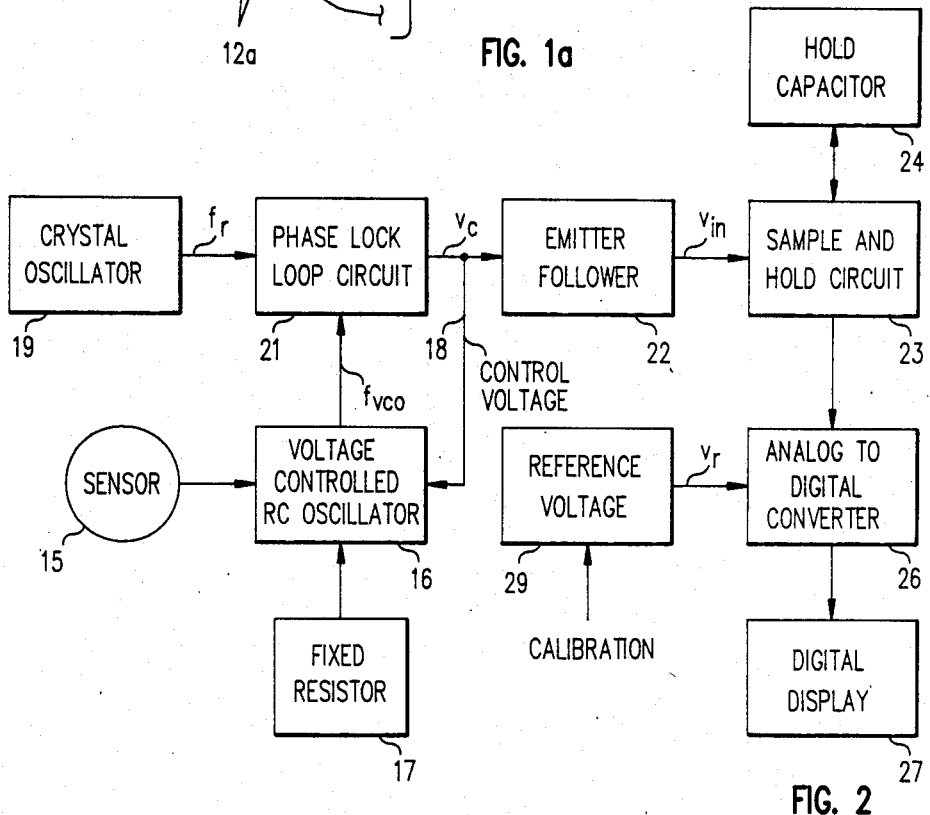
FIG. 2 is a schematic block diagram of circuitry for implementing the present invention.

A schematic block diagram of the fluid analyzer is shown in FIG. 2. The sensor 15 described above, including plates 12a, 12b and substrate 13, is used as the capacitance element in an RC voltage controlled oscillator 16 whose output frequency is determined by a fixed resistor 17, the sensor capacitance and the level of the control voltage $V_C$ supplied to oscillator 16 on a line 18. An accurate known reference frequency $F_R$, is generated by a crystal oscillator 19.

Both the reference frequency and the voltage controlled oscillator frequency are fed to a phase comparator phase lock loop circuit 21. This circuit produces an output error voltage $V_C$ which, when applied to the input of the voltage controlled oscillator 16, is exactly sufficient to cause the oscillator 16 to oscillate at the reference frequency.

Thus, the magnitude of the control voltage, $V_C$, is directly proportional to the difference between the reference frequency and the free running VCO frequency. As a consequence, this control voltage is directly proportional to the sensor capacitance. The control voltage output is isolated from loading effects of subsequent circuits by an emitter follower 22 or operational amplifier.

The sample and hold circuit 23 connected to the output of emitter follower 22 charges a low leakage capacitor 24 to a given reference voltage, $V_{IN}$, when the reference fluid is introduced into the sensor well and the user initiates the charging process, through a pushbutton switch. When the sensor is cleaned of the reference fluid and the fluid to be analyzed is introduced into the sensor, a new $V_{IN}$ will result.

The $V_{IN}$ from the test fluid is compared to the $V_{IN}$ from the reference fluid, which has been stored by the sample and hold capacitor 24, in the analog to digital conversion circuitry 26. The difference between these two voltages is proportional to the difference in dielectric constant between the two fluids. Either high accuracy dual slope integration or a succesive approximation circuitry may be used for the analog to digital conversion process. A prototype digital fluid analyzer utilizes a high accuracy 3½ digit slope integration LSI integrated circuit to perform this function.

A circuit for calibration of the resulting value of the display, based upon its relation to a known reference voltage provided from circuitry 29, is provided. The output of the circuit is a digital readout, on a device 27, such as a 3½ digit liquid crystal (LCD) or LED display, whose numerical reading is a direct indication of the difference in dielectric constant between the reference fluid and the fluid to be tested.

Thus, the present invention, unlike that shown in the Roof et al. patent discussed above, provides for sequential testing of a reference fluid and a sample fluid, thereby reducing the circuitry required in comparison to the simultaneous analysis of a reference fluid and a sample fluid as in Roof et al.

I claim:

1. Apparatus for determining the amount of contamination in a fluid, comprising:

a test cell sensor for receiving fluid samples, said test cell sensor including a capacitive element between whose plates a fluid sample is located when one of said samples is in said test cell;

a voltage controlled RC oscillator circuit, said capacitive element in said sensor forming the capacitive portion of said RC oscillator circuit;

a phase lock loop circuit producing an output signal which is a measure of the dielectric constant of the fluid sample in said test cell; and comparing means connected to said phase lock loop circuit for comparing said phase lock loop output signals to provide a measure of the difference in dielectric constants of the tested fluids, said difference being an indication of the degree of contamination of one of said fluids;

said comparing means including sample and hold circuitry for storing a signal representing a measure of the dielectric constant of the first tested fluid.

2. Apparatus in accordance with claim 1 in which said comparing means includes an analog-to-digital converter responsive to the output of said sample and hold circuitry.

* * * * *